(12) United States Patent
Arbiser (10) Patent No.: US 8,691,777 B2
(45) Date of Patent: Apr. 8, 2014

(54) COMBINATION THERAPY

(75) Inventor: Jack L. Arbiser, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 13/357,920

(22) Filed: Jan. 25, 2012

(65) Prior Publication Data

US 2012/0196870 A1 Aug. 2, 2012

Related U.S. Application Data

(60) Provisional application No. 61/436,760, filed on Jan. 27, 2011.

(51) Int. Cl.
*A61K 31/70* (2006.01)
*A61K 31/535* (2006.01)
*A61K 31/497* (2006.01)

(52) U.S. Cl.
USPC ............... 514/31; 514/235.8; 514/252.11; 514/252.18

(58) Field of Classification Search
USPC .............. 514/31, 252.11, 235.8, 252.18
See application file for complete search history.

(56) References Cited

U.S. PATENT DOCUMENTS

| | | | |
|---|---|---|---|
| 5,521,184 A * | 5/1996 | Zimmermann | 514/252.11 |
| 6,369,086 B1 | 4/2002 | Davis et al. | |
| 6,369,087 B1 | 4/2002 | Whittle et al. | |
| 6,372,733 B1 | 4/2002 | Caldwell et al. | |
| 6,372,778 B1 | 4/2002 | Tung et al. | |

FOREIGN PATENT DOCUMENTS

| | | | |
|---|---|---|---|
| WO | WO 2008094181 A2 * | 8/2008 | |
| WO | 2008/109163 | 9/2008 | |

OTHER PUBLICATIONS

Lee et al., "Rapamycin weekly maintenance dosing and the potential efficacy of combination sorafenib plus rapamycin but not atorvastatin o doxycycline in tuberous sclerosis preclinical models", BMC Pharmacology, vol. 9, pp. 1-15 (2009).*
Bissler, J., et al. 2008, Sirolimus for angiomyolipoma in tuberous sclerosis complex or lymphangioleiomyomatosis. N Engl J Med., 358(2):pp. 140-151.
Franz, D.N. et al., 2006, Rapamycin causes regression of astrocytomas in tuberous sclerosis complex. Ann Neurol.., 59(3): pp. 490-498.
Merimsky, O. et al., 2007, Molecular impacts of rapamycin-based drug combinations: Combining rapamycin with gemcitabine or imatinib mesylate (Gleevec) in a human leiomyosarcoma model, Int J Oncol., 31(1):pp. 225-332.
Tsai, , P., 2011, Mechanisms of neurocognitive dysfunction and therapeutic considerations in tuberous sclerosis complex. Curr Opin Neurol. 24(2): pp. 106-113.

* cited by examiner

*Primary Examiner* — Kevin E Weddington
(74) *Attorney, Agent, or Firm* — Emory Patent Group; James C. Mason; Susanne Hollinger (57) ABSTRACT

The disclosure relates to methods of treating tuberous sclerosis in a subject, comprising administering a composition comprising an mTOR inhibitor and a tyrosine kinase inhibitor to a subject that is diagnosed with, suspected of, or exhibiting symptoms of cancer. In some embodiments, the cancer is tuberous sclerosis. In some embodiments, the mTOR inhibitor is sirolimus and the tyrosine kinase inhibitor is imatinib. In some embodiments, the disclosure relates to a composition comprising an mTOR inhibitor and a tyrosine kinase inhibitor. In some embodiments, the disclosure relates to a composition comprising sirolimus and imatinib.

6 Claims, 7 Drawing Sheets

Fold change up-regulated

Molecules | | Exp.Value
---|---|---
PRELP | Proline/arginine-rich end leucine-rich repeat protein | 5.070
SLC1A3 | Solute carrier family 1, member 3 | 3.754
ACTA2 | Actin, alpha 2, smooth muscle, aorta | 3.518
FST | Follistatin | 2.873
GAS6 | Growth arrest-specific 6 | 2.818
CRLF1 | Cytokine receptor-like factor 1 | 2.780
CXCL12 | Chemokine (C-X-C motif) ligand 12 | 2.519
PORCN | Porcupine homolog | 2.339
NBL1 | Neuroblastoma, suppression of tumorigenicity 1 | 2.318
MMP11 | Matrix metallopeptidase 11 (stromelysin 3) | 2.241

FIGURE 4A

Fold down regulated

Molecules | | Exp.Value
---|---|---
CCNB1 | cyclin B1 | 8.414
CENPA | centromere protein A | 6.954
BIRC5 | Baculoviral IAP repeat-containing 5 | 6.153
HIST1H2AH | Histone cluster 1, H2ah | 6.091
PRC1 | protein regulator of cytokinesis 1 | 5.859
AURKA | Aurora kinase A | 5.544
PBK | PDZ binding kinase | 5.114
AURKB | Aurora kinase B | 5.013
HIST1H2AD | Histone cluster 1, H2ad | 4.879
PLK1 | polo-like kinase 1 | 4.768

COMBINATION THERAPY

CROSS REFERENCE TO RELATED APPLICATIONS

This application claims priority to U.S. Provisional Application No. 61/436,760 filed Jan. 27, 2011, which application is hereby incorporated by this reference in its entirety.

ACKNOWLEDGEMENTS

This invention was made with government support under Grants RO1-AR47901, P30-AR42687, CA87986, CA116552 and CA99163 awarded by the National Institutes of Health. The government has certain rights in the invention.

FIELD

The disclosure relates to methods of treating tuberous sclerosis in a subject, comprising administering a composition comprising an mTOR inhibitor and a tyrosine kinase inhibitor to a subject that is diagnosed with, suspected of, or exhibiting symptoms of cancer. In some embodiments, the cancer is tuberous sclerosis. In some embodiments, the mTOR inhibitor is sirolimus and the tyrosine kinase inhibitor is imatinib. In some embodiments, the disclosure relates to a composition comprising an mTOR inhibitor and a tyrosine kinase inhibitor. In some embodiments, the disclosure relates to a composition comprising sirolimus and imatinib.

BACKGROUND

Tuberous Sclerosis (TS) is an autosomal dominant disorder that is characterized by the development of benign and malignant tumors of the brain, kidney, lung, and skin. TS is characterized by mutations or deletions in one of two genes, either hamartin (tsc1) or tuberin (tsc2). Furthermore, TS is associated with neuro-developmental complications, including autism and seizures, leading to significant morbidity. Although there is no known strict genotype-phenotype relationship with TS, the disease is more severe in patients with tsc2 mutations. Loss of heterozygosity, in which the unaffected allele is deleted, is necessary for the development of certain neoplastic features of TS, including renal angiomyolipomas, lymphangiomyomatosis, and skin lesions.

TS is associated with a number of complex signaling pathways. Tsc2 mutations often involve regions implicated in controlling rheb, although other signaling pathways have been implicated in TS-related neoplasia, including mTORC1, notch, p42/44 MAP kinase, NFkB, and Akt. The use of sirolimus as a therapy for TS has been based on the upregulation of mTORC1 in the neoplasms of TS patients. Although sirolimus resulted in a partial regression of kidney, lung and skin lesions, there was not a complete disappearance of tumors. See, e.g., Franz, D. N. et al. Rapamycin causes regression of astrocytomas in tuberous sclerosis complex. Ann Neurol. 2006 March; 59(3):490-8. Furthermore, tumor regrowth was observed upon cessation of sirolimus therapy. Bissler, J J. et al. Sirolimus for angiomyolipoma in tuberous sclerosis complex or lymphangioleiomyomatosis. N Engl J Med. 2008 Jan. 10; 358(2):140-51. These clinical observations indicate that other signaling pathways may be active in TS-related tumors.

SUMMARY

The disclosure relates to methods of treating tuberous sclerosis in a subject, comprising administering a composition comprising an mTOR inhibitor and a tyrosine kinase inhibitor to a subject that is diagnosed with, suspected of, or exhibiting symptoms of cancer. In some embodiments, the cancer is tuberous sclerosis. In some embodiments, the mTOR inhibitor in the method or composition is Sirolimus, Everolimus, Deforolimus, AZD8055, BEZ235, GSK1059615, KU-0063794, WYE-354, PI-103, Temsirolimus, Ridaforolimus, Zotarolimus, and Umirolimus (also known as Biolimus or Biolimus A9). In some embodiments, the tyrosine kinase inhibitor in the method or composition is imatinib, linifanib, ponatinib, regorafenib, vargatef, or sunitinib, or CP 673451. In some embodiments, the disclosure relates to a composition comprising an mTOR inhibitor and a tyrosine kinase inhibitor. In some embodiments, the disclosure relates to a composition comprising sirolimus and imatinib.

In some embodiments, the administration of the composition is performed under conditions such that the tuberous sclerosis is no longer detected. In some embodiments, the disclosure relates to treating or preventing tuberous sclerosis by administering an mTOR inhibitor and a tyrosine kinase inhibitor to a subject also diagnosed with another type of cancer. In some embodiments, the subject is diagnosed with a mutation in hamartin (tsc1) or tuberin (tsc2).

In some embodiments, the subject is diagnosed with tuberous sclerosis, skin cancer, breast cancer, prostate cancer, lung cancer, bladder cancer, melanoma, colon and rectal cancer, non-hodgkin's lymphoma, endometrial cancer, pancreatic cancer, renal cell cancer, leukemia, and/or thyroid cancer.

In some embodiments, the subject is a mammal, typically a human.

In some embodiments, the tyrosine kinase inhibitor is a platelet-derived growth factor receptor (PDGFR) inhibitor. In some embodiments, the tyrosine kinase inhibitor is an Abelson (Abl) protein inhibitor. In some embodiments, the tyrosine kinase inhibitor is a CD117 (Mast/stem cell growth factor receptor) inhibitor. In some embodiments, the tyrosine kinase inhibitor is imatinib, linifanib, ponatinib, regorafenib, vargatef, or sunitinib, or CP 673451. In some embodiments, the disclosure may include therapeutic methods and compositions targeting the active site of the TK domain in abl (the Abelson proto-oncogene), c-kit, and PDGF-R (platelet-derived growth factor receptor).

In some embodiments, the subject undergoes immunological monitoring. In some embodiments, the disclosure relates to methods of treating a subject diagnosed with tuberous sclerosis and either treating or preventing a viral infection by administration of an mTOR inhibitor, a tyrosine kinase inhibitor, and one or more anti-viral agents, wherein the subject is immunocompromised. In typical embodiments, the immunocompromised subject is an organ transplant recipient, undergoing hemodialysis, diagnosed with cancer, receiving an immunosuppressive drug, and/or diagnosed with an HIV-infection. In some embodiments, the subject is at risk of an infection because the sexual partner of the subject is diagnosed with a virus.

In some embodiments, the subject is diagnosed with influenza A virus including subtype H1N1, influenza B virus, influenza C virus, rotavirus A, rotavirus B, rotavirus C, rotavirus D, rotavirus E, SARS coronavirus, human adenovirus types (HAdV-1 to 55), human papillomavirus (HPV) Types 16, 18, 31, 33, 35, 39, 45, 51, 52, 56, 58, 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, Kaposi's sarcoma-associated herpesvirus, hepatitis A (HAV), hepatitis B (HBV), hepatitis C (HCV), hepatitis D (HDV), hepatitis E (HEV), human immunodeficiency virus (HIV), The Human T-lymphotropic virus Type I (HTLV-1), Friend spleen focus-forming virus (SFFV) or Xenotropic MuLV-Related Virus (XMRV).

In some embodiments, the subject is diagnosed with a virus, as described above, and is administered a pharmaceutical composition comprising sirolimus, imatinib, and an antiviral agent. The antiviral agent may be abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex), valganciclovir, vicriviroc, vidarabine, viramidine zalcitabine, zanamivir (Relenza), and/or zidovudine.

In some embodiments, the subject is diagnosed or susceptible to a bacterial infection. In some embodiments, the subject is administered one or more antibiotics including, but not limited to, Sulfonamides, Diaminopyrimidines, Quinolones, Beta-lactam antibiotics, Cephalosporins, Tetracyclines, Notribenzene derivatives, Aminoglycosides, Macrolide antibiotics, Polypeptide antibiotics, Nitrofuran derivatives, Nitroimidazoles, Nicotinin acid derivatives, Polyene antibiotics, Imidazole derivatives or Glycopeptide, Cyclic lipopeptides, Glycylcyclines and Oxazolidinones. In further embodiments, these antibiotics include but are not limited to Sulphadiazine, Sulfones—[Dapsone (DDS) and Paraaminosalicyclic (PAS)], Sulfanilamide, Sulfamethizole, Sulfamethoxazole, Sulfapyridine, Trimethoprim, Pyrimethamine, Nalidixic acids, Norfloxacin, Ciproflaxin, Cinoxacin, Enoxacin, Gatifloxacin, Gemifloxacin, Grepafloxacin, Levofloxacin, Lomefloxacin, Moxifloxacin, Ofloxacin, Pefloxacin, Sparfloxacin, Trovafloxacin, Penicillins (Amoxicillin, Ampicillin, Azlocillin, Carbenicillin, Cloxacillin, Dicloxacillin, Flucloxacillin, Hetacillin, Oxacillin, Mezlocillin, Penicillin G, Penicillin V, Piperacillin), Cephalosporins (Cefacetrile, Cefadroxil, Cefalexin, Cefaloglycin, Cefalonium, Cefaloridin, Cefalotin, Cefapirin, Cefatrizine, Cefazaflur, Cefazedone, Cefazolin, Cefradine, Cefroxadine, Ceftezole, Cefaclor, Cefonicid, Ceforanide, Cefprozil, Cefuroxime, Cefuzonam, Cefmetazole, Cefoteta, Cefoxitin, Cefcapene, Cefdaloxime, Cefdinir, Cefditoren, Cefetamet, Cefixime, Cefmenoxime, Cefodizime, Cefoperazone, Cefotaxime, Cefotiam, Cefpimizole, Cefpiramide, Cefpodoxime, Cefteram, Ceftibuten, Ceftiofur, Ceftiolen, Ceftizoxime, Ceftriaxone, Cefoperazone, Ceftazidime, Cefepime), Moxolactam, Carbapenems (Imipenem, Ertapenem, Meropenem) Monobactams (Aztreonam), Oxytetracycline, Chlortetracycline, Clomocycline, Demeclocycline, Tetracycline, Doxycycline, Lymecycline, Meclocycline, Methacycline, Minocycline, Rolitetracycline, Chloramphenicol, Amikacin, Gentamicin, Framycetin, Kanamycin, Neomicin, Neomycin, Netilmicin, Streptomycin, Tobramycin, Azithromycin, Clarithromycin, Dirithromycin, Erythromycin, Roxithromycin, Telithromycin, Polymyxin-B, Colistin, Bacitracin, Tyrothricin Notrifurantoin, Furazolidone, Metronidazole, Tinidazole, Isoniazid, Pyrazinamide, Ethionamide, Nystatin, Amphotericin-B, Hamycin, Miconazole, Clotrimazole, Ketoconazole, Fluconazole, Rifampacin, Lincomycin, Clindamycin, Spectinomycin, Chloramphenicol, Clindamycin, Colistin, Fosfomycin, Loracarbef, Metronidazole, Nitrofurantoin, Polymyxin B, Polymyxin B Sulfate, Procain, Spectinomycin, Tinidazole, Trimethoprim, Ramoplanin, Teicoplanin, Vancomycin, Trimethoprim, Sulfamethoxazole, and/or Nitrofurantoin.

BRIEF DESCRIPTION OF THE FIGURES

FIG. 4. A. List of genes with greatest change in sirolimus-treated vs. control cells. B. List of genes with greatest change in sirolimus-treated vs. combination therapy-treated cells.

FIG. 5. Relative expression levels of A. Aurora kinase A, B. Aurora kinase B, C. Centromere protein A in tsc2ang1 cells. D. Western blot analysis comparing therapies.

DETAILED DESCRIPTION mTOR Inhibitor

As used herein, "mTOR" inhibitor refers to any therapeutic capable of inhibiting the mammalian target of rapamycin. Typically, the mTOR inhibitor is sirolimus. As used herein, "sirolimus" may refer to sirolimus (also known as rapamycin) or any formulation (e.g. Rapamune), functional equivalent, or derivative thereof Functional equivalents and derivatives may include other mammalian target of rapamycin (mTOR) inhibitors including, but not limited to, Everolimus, Deforolimus, AZD8055, BEZ235, GSK1059615, KU-0063794, WYE-354, PI-103, Temsirolimus, Ridaforolimus, Zotarolimus, and Umirolimus (also known as Biolimus or Biolimus A9).

Sirolimus is a type of macrolide (i.e. possesses a ringed chemical structure) first isolated from bacteria found on Rapa Nui (Easter Island). Sirolimus is currently used as an antiproliferative agent in cancer as well as an immunosuppressant and may act by inhibiting cell cycle progression. In particular, sirolimus has shown promise in the treatment of TS, but remains problematic as a monotherapy due to the return of TS following cessation of sirolimus therapy. See, e.g., Tsai, P. Mechanisms of neurocognitive dysfunction and therapeutic considerations in tuberous sclerosis complex. Curr Opin Neurol. 2011 April; 24(2):106-13.

As disclosed herein, sirolimus monotherapy may induce PDGFR signaling, as well as upregulate Aurora kinase signaling, thus providing a rationale for the failure of sirolimus monotherapy in tuberous sclerosis. Platelet-derived growth factor $\beta$ receptor (PDGFR $\beta$) is both present and active in human and murine TS lesions. There is an inverse relationship between mTOR activation and the PDGFR$\beta$ levels in TSderived cells. Therefore, mTOR blockade might be compensated for by a PDGF activator, such as imatinib, both in vitro and in vivo.

Tyrosine Kinase Inhibitor

As used herein, the term "tyrosine kinase inhibitor" may refer to any tyrosine kinase inhibitor. The tyrosine kinase inhibitor may be a platelet-derived growth factor receptor (PDGFR) inhibitor, an Abelson (Abl) protein inhibitor, or a CD117 inhibitor. Tyrosine kinase inhibitors include, but are not limited to, imatinib, linifanib, ponatinib, regorafenib, vargatef, or sunitinib, or CP 673451. Typically, the tyrosine kinase inhibitor is imatinib. As used herein, the term "imatinib" may refer to imatinib or any formulation (e.g. Gleevec or Glivec, a mesylate salt formulation), functional equivalent, or derivative thereof. Imatinib is a tyrosine kinase (TK) enzyme inhibitor, acting by occupying the TK active site thereby diminishing TK activity. Functional equivalents may include therapeutics targeting the active site of the TK domain in abl (the Abelson proto-oncogene), c-kit, and PDGF-R (platelet-derived growth factor receptor).

Tuberous Sclerosis

"Tuberous sclerosis" (TS) refers to a multisystem disorder characterized by benign and malignant neoplasia, in some instances autism and seizures. No effective therapy currently exists for TS. Renal lesions such as angiomyolipomas may cause massive bleeding and compromise renal function, often requiring a kidney transplant. Lymphangiomyomatosis, a neoplastic complication most commonly seen in young women, can only be cured by lung transplantation. Such transplantation is itself problematic, requiring immunosuppression and typically failing within approximately five years. Deforming skin lesions cause significant psychological distress. Brain tumors, such as subependymal giant cell astrocytomas, can cause morbidity and mortality, and multiple tubers result in refractory seizures and exacerbation of mental retardation. These complications demonstrate that effective therapy for TS is urgently needed. TS may also refer to a subject diagnosed with other forms of cancer in addition to TS.

Multiple signaling pathways are impacted by mutations in tsc1 and tsc2. One of the most well studied pathways is rheb, a ras like protein which is inhibited by the heterodimer of tsc1/tsc2. If rheb is activated, then, mTORC1 and notch are activated downstream, but notch activation is independent of mTORC1 because notch activation is not blocked by sirolimus. The lack of total blockade by sirolimus is consistent with the incomplete clinical response of tumors to systemic sirolimus, implying that either additional pathways are already present in these tumors or are induced by sirolimus monotherapy. High among the candidate pathways is a PDGFRβ-mediated pathway, especially since mTORC1 activation and PDGFRβ signaling have been shown to have an inverse relationship.

Combination Therapy

In some embodiments, the disclosure relates to treating Tuberous Sclerosis with combination therapy comprising a composition comprised of an mTOR inhibitor, typically sirolimus, and a tyrosine kinase inhibitor, typically imatinib. The combination of sirolimus and imatinib, two FDA-approved drugs, is well tolerated in vivo. Given that sirolimus monotherapy does not cause long lasting remissions in tuberous sclerosis, as disclosed herein, a rationale exists for the combination of these two drugs in humans.

One previous study tested sirolimus and imatinib when using SK-LMS-1 cells as a model for human leiomyosarcoma. That study, however, explicitly stated that there was no advantage to adding imatinib to the sirolimus monotherapy. Merimsky, O. et al. Molecular impacts of rapamycin-based drug combinations: Combining rapamycin with gemcitabine or imatinib mesylate (Gleevec) in a human leiomyosarcoma model. Int J Oncol. 2007 July; 31(1):225-32. Sirolimus and imatinib in a nanoparticle formulation with an albumin carrier protein has been suggested as part of a list of numerous potential combinations, for the treatment of cancer. No demonstration of its utility in TS, which was listed among more than 100 other forms of cancer, was presented. Published International Patent Application WO 2008/109163 A1.

Formulations

Generally, for pharmaceutical use, the compositions may be formulated as a pharmaceutical preparation comprising an mTOR inhibitor, typically sirolimus, in combination with a tyrosine kinase inhibitor, typically imatinib.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 40 mg, and usually between 2 and 6 mg, of the mTOR inhibitor, typically sirolimus, e.g. about 2 mg per unit dosage, and 1 and 1000 mg. A one-time bolus, of sirolimus for example, may be given initially followed by lower subsequent doses, e.g. 6 mg on day one followed by 2 mg per day thereafter. The unit dosage is usually between 100 and 800 mg of the tyrosine kinase inhibitor, typically imatinib, e.g. about 10, 25, 50, 100, 200, 300, 400, or 800 mg per unit dosage.

The compositions can be administered by a variety of routes including the oral, ocular, rectal, transdermal, subcutaneous, intravenous, intramuscular or intranasal routes, depending mainly on the specific formulation used. Typically, the mTOR inhibitor is administered orally, either in pill or liquid formulations. Typically, the tyrosine kinase inhibitor is administered orally in pill form. The composition will generally be administered in an "effective amount", by which is meant any amount of a composition that, upon suitable administration, is sufficient to achieve the desired therapeutic or prophylactic effect in the subject to which it is administered. Depending on the condition to be prevented or treated and the route of administration, an effective amount of either the mTOR inhibitor or tyrosine kinase inhibitor may be determined by the subject's body weight. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. No. 6,372,778, U.S. Pat. No. 6,369,086, U.S. Pat. No. 6,369,087 and U.S. Pat. No. 6,372,733 as well as to standard handbooks, such as the latest edition of Remington's Pharmaceutical Sciences.

For an oral administration form, the composition can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. Oily excipients or solvents are vegetable or animal oils, such as sunflower oil or cod liver oil. Solvents for aqueous or alcoholic solutions are water, ethanol, sugar solutions, or mixtures thereof Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compositions of the disclosure or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the compositions, if desired with the substances customary therefore such as solubilizers, emulsifiers or further auxiliaries are brought into solution, suspension, or emulsion. The compositions can also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compositions with a suitable non-irritating excipient, such as cocoa butter, synthetic glyceride esters or polyethylene glycols, which are solid at ordinary temperatures, but liquefy and/or dissolve in the rectal cavity to release the drug.

In some embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaluronic acid, chitin, chitosan and the like; other natural polymers, such as proteins (albumin, gelatin etc.), poly-L-lysine; sodium poly(acrylic acid); poly(hydroxyalkylmethacrylates) (for example poly (hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethylcellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxy groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Administration of the therapies described herein may include a method of sustained release. Sustained release may be achieved in multiple ways known to one ordinarily skilled in the art. These methods include, but are not limited to, implantable osmotic pumps and formulations of sirolimus and/or imatinib that are not soluble at physiological pH, resulting in the gradual dissolving after, for example, injection.

Aurora Kinases

Aurora kinases are a family of serine/threonine kinases that are necessary for mitosis and meiosis. Aurora kinases A and B are the most prominent. Although there are structural similarities between Aurora kinases A and B, each has a different role in both cytokinesis and tumorigenesis. The activation of Aurora kinases is required for the optimal growth of tumor cells. Furthermore, different tumors appear to have differential sensitivity to Aurora kinase inhibitors. The amplification of Aurora kinase A is associated with highly aneuploid tumors as well as p53 dysfunction, whereas Aurora kinase B is highly associated with tumors with wild type p53.

Terms

As used herein, the term "immunocompromised" or "immunosuppressed" refers to a subject with an impaired or ablated immune response. The impairment or ablation may be complete or partial. Partial immunosuppression may or may not result in the inability to mount an appropriate immune response. Typically, immunocompromised refers to the depletion of a particular cell type, such as lymphocytes. A subject may be immunocompromised, for example, by taking immunosuppressive drugs in order to prevent allograft rejection Immunosuppressive drugs include, but are not limited to, antithymocyte globulin (ATG), ATG-fresenius, anti-CD3 monoclonal antibody (mAb), anti-CD20 mAb, anti-TNF mAb, sirolimus, anti-CD25 mAb, and calcineurin inhibitors (e.g. cyclosporine).

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing a oxygen atom with a sulfur atom or replacing a amino group with a hydroxyl group. The derivative may be a prodrug. Derivatives may be prepare by any variety of synthetic methods or appropriate adaptations presented in synthetic or organic chemistry text books, such as those provide in March's Advanced Organic Chemistry:

Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—CH3).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above with the indicated number of carbon atoms attached through an amino bridge. An example of an alkylamino is methylamino, (i.e., —NH—CH3).

"Alkanoyl" refers to an alkyl as defined above with the indicated number of carbon atoms attached through a carbonyl bride (i.e., —(C=O)alkyl).

"Alkylsulfonyl" refers to an alkyl as defined above with the indicated number of carbon atoms attached through a sulfonyl bridge (i.e., —S(=O)2alkyl) such as mesyl and the like, and "Arylsulfonyl" refers to an aryl attached through a sulfonyl bridge (i.e., —S(=O)2aryl).

"Alkylsulfamoyl" refers to an alkyl as defined above with the indicated number of carbon atoms attached through a sulfamoyl bridge (i.e., —NHS(=O)2alkyl), and an "Arylsulfamoyl" refers to an alkyl attached through a sulfamoyl bridge (i.e., (i.e., —NHS(=O)2aryl).

"Alkylsulfinyl" refers to an alkyl as defined above with the indicated number of carbon atoms attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

The terms "cycloalkyl" and "cycloalkenyl" refer to mono-, bi-, or tri homocyclic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g., fluorene, tetrahydronapthalene, dihydroindene, and the like). The rings of multi-ring cycloalkyl groups may be either fused, bridged and/or joined through one or more spiro unions. The terms "substituted cycloalkyl" and "substituted cycloalkenyl" refer, respectively, to cycloalkyl and cycloalkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The terms "halogen" and "halo" refer to fluorine, chlorine, bromine, and iodine. An unspecified "R" group is a hydrogen, lower alkyl, or aryl all of which may be optionally substituted with one or more substituents. Throughout the specification, groups and substituents thereof may be chosen to provide stable moieties and compounds.

The terms "treatment" or "treating" include any desirable effect on the symptoms or pathology of tuberous sclerosis, and may include even minimal reductions in one or more measurable markers of the disease or condition. "Treatment" does not necessarily indicate complete eradication or cure of tuberous sclerosis, or associated symptoms thereof. The subject receiving this treatment is any animal in need, including primates, typically humans, and other mammals such as equines, cattle, swine and sheep as well as poultry and other pets.

In some embodiments, the subject has a compromised or suppressed immune system. Immunosuppression reduces the activation or efficacy of the immune system. Deliberately induced immunosuppression is typically done to prevent the body from rejecting an organ transplant (e.g., bone marrow, heart, kidney, liver), treating graft-versus-host disease after a bone marrow transplant, or for the treatment of auto-immune diseases (e.g., rheumatoid arthritis, multiple sclerosis, myasthenia gravis, systemic lupus erythematosus, Crohn's disease, pemphigus, and ulcerative colitis). Depending on the dose used, the mTOR described herein may result in detectable immunosuppression, via the induction of regulatory T lymphocytes by sirolimus for example Immunosuppression may be accomplished by certain agents (immunosuppressants) such as, but not limited to, dactinomycin, azathioprine, mycophenolic acid, leflunomide, teriflunomide, methotrexate, tacrolimus, ciclosporin, pimecrolimus, abetimus, gusperimus, lenalidomide, anakinra, sirolimus, deforolimus, everolimus, temsirolimus, zotarolimusm, biolimus A9, antithymocyte globulin (ATG), T-cell receptor directed antibodies (e.g., muromonab), and IL-2 receptor directed antibodies (e.g., basiliximab and daclizumab). Surgery (splenectomy), plasmapharesis, or radiation may also cause a suppressed immune system. Since certain immunosuppressants act nonselectively, the immune system may be less able to combat tumorogenesis. A person who is undergoing immunosuppressant therapy, or whose immune system is weak for other reasons (for example, chemotherapy, HIV, and Lupus) is said to be immunocompromised. Neonates are considered to immunocompromised. Certain viruses such as HIV will comprise the host immune system. In some embodiments, the disclosure relates to treating or preventing Tuberous Sclerosis by administering sirolimus and imatinib combination therapy to an immunocompromised subject.

As used herein, the term "combination with" or "combination therapy" when used to describe administration of an mTOR inhibitor and a tyrosine kinase inhibitor means that either agent may be administered prior to, together with, or after the other agent, or a combination thereof.

As used herein, the term "subject" refers to any animal, preferably a human patient, livestock, or domestic pet.

EXPERIMENTAL

Example 1

Sirolimus and Imatinib Combination Therapy Inhibits TSC2 Cell Proliferation

Figure 1:
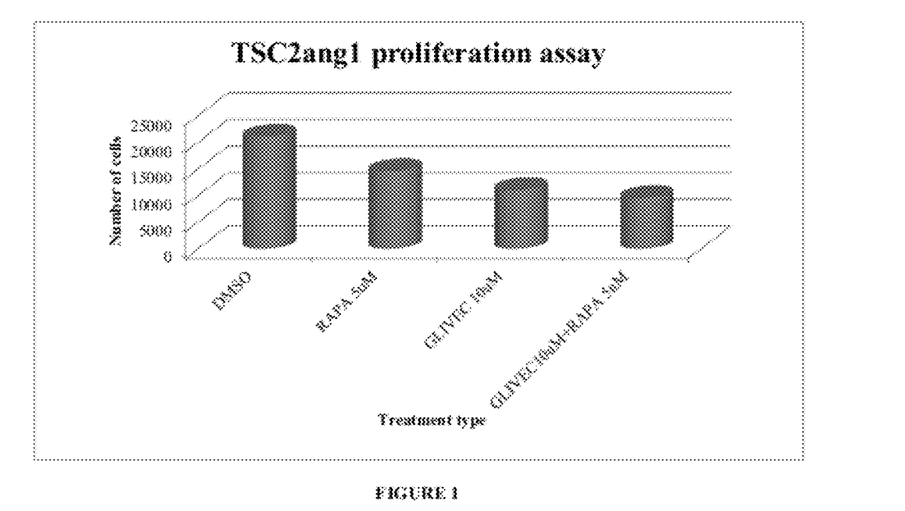
FIG. 1. Effect of sirolimus, imatinib or combination of sirolimus and imatinib on tsc2ang1 cell line proliferation.

A proliferation assay with Tsc2 cells indicated a decrease in the viable cell numbers when treated independently with either rapamycin (5 nM) or imatinib (10 μM) for 24 hours. $10^4$ tsc2ang1 cells per well were plated in 24-well dishes in triplicate. The next day, fresh medium containing the compounds or vehicle controls was added. Cells were incubated at 37° C. Tsc2ang1 (ATCC CRL 2620) is a murine cell line derived from a cutaneous sarcoma that arose in the extremity of a mouse heterozygous for tsc2; these mice develop cutaneous sarcomas at a frequency of about 10 to 15%. The cells were cultured in complete DMEM medium supplemented with 10% FBS (Sigma Aldrich, St Louis, Mo.). Combination treatment of rapamycin (5 nM) and imatinib (10 μM) showed a significant decrease in the viable cell number compared with DMSO treated control cells (FIG. 1). Cells were treated with vehicle control (DMSO), rapamycin (5 nM), imatinib (10 μM) or imatinib (10 μM)+rapamycin (5 nM) (shown along X-axis) for 24 h and counted using a Coulter counter. The Y-axis represents cell number with error bars representing the SEM. The effect of imatinib and rapamycin in combination was significantly different than either rapamycin ($p<0.05$) or imatinib ($p<0.05$) monotherapy.

Example 2

Figure 2:
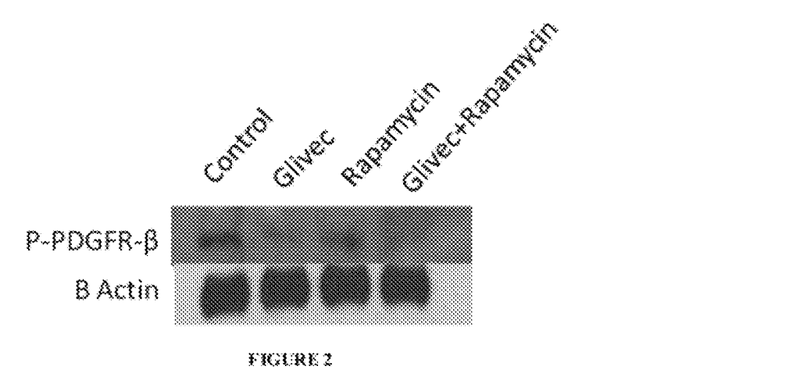
FIG. 2. Phospho-PDGFR-$\beta$ is strongly downregulated in combinational treatment.

Sirolimus and Imatinib Combination Therapy Inhibits Activation of PDGFRβ Tsc2 ang1 Cells The impact of imatinib (10 μm), rapamycin (10 nM), and a combination of rapamycin and imatinib on the phosphorylated PDGFR-β signaling pathway was tested in Tsc2ang1cells. Treatment of tsc2ang1 cells with rapamycin monotherapy led to upregulation of PDGFR β and increased phosphorylation at Tyr-1009 compared with DMSO control Imatinib treatment, however, led to a downregulation of PDGFR β phosphorylation; this decrease was maintained in the presence of rapamycin (FIG. 2). The upregulation of PDGFRβ by rapamycin monotherapy suggests that the activation of PDGFRβ is a compensatory mechanism to the mTOR blockade.

Example 3

Sirolimus and Imatinib Combination Therapy's Effect on Angiogenic Mediators

Figure 3A:
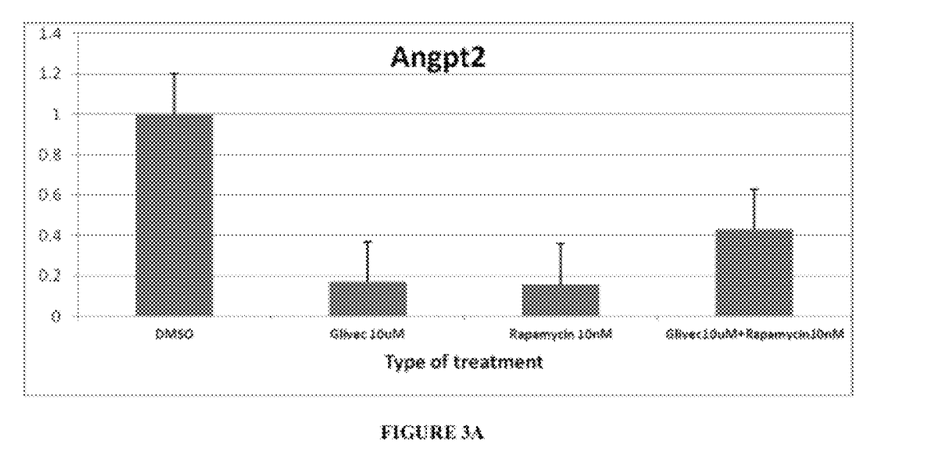
FIG. 3. Combination therapy significantly downregulates Angpt2, Nrarp, and VEGF.
Figure 3B:
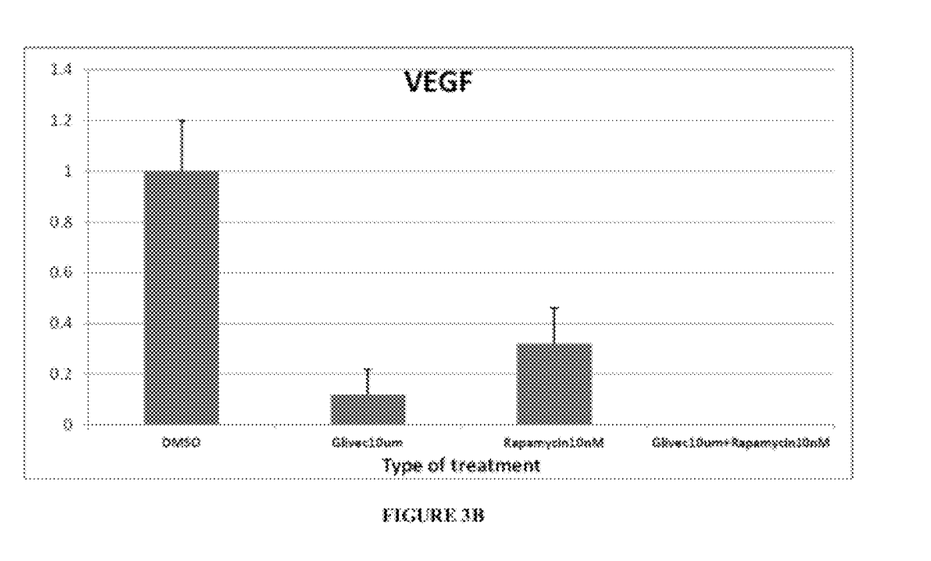
Figure 3C:
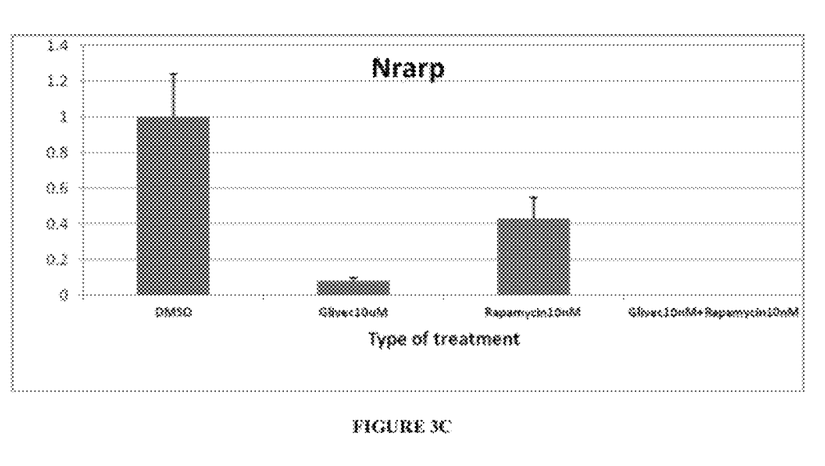

Tsc2ang1 cells were treated with control (DMSO), rapamycin (5 nM), imatinib (10 μM), and imatinib (10 μM)+rapamycin (5 nM) for 24 hours. Total RNA was then extracted and the levels of expression of the angiogenic genes Angiopoietin-2 (Angpt2) (FIG. 3a), NOTCH-regulated ankyrin repeat protein (Nrarp) (FIG. 3c), and Vascular endothelial growth factor (VEGF) (FIG. 3b) were measured by real-time PCR. Significant downregulation of Angpt2 ($p<0.001$), Nrarp ($p<0.001$), and VEGF ($p<0.05$) levels were observed in the imatinib (10 µM)+rapamycin (5 nM) combination therapy group. Total RNA was extracted from cell pellets pooled from two identical and independent experiments using the RNeasy mini column (Qiagen). 10 µg total RNA pools from different experimental conditions were independently and randomly labeled with either Cy3 or Cy5 fluorophores using the Agilent Fluorescent Direct Label kit (Agilent Technologies). Labeled RNA pools were then competitively hybridized to Agilent murine cDNA microarray slides, which contain 2 identical array areas. The above procedures were repeated 3 times on RNA isolated from a different batch of cells, giving 6 arrays in an n=3 (biological replicates), n=2 (technical replicates) arrangement for each comparison group. Fluorescence intensities of each hybridized spot were determined by using the Agilent Array Scanner and the Agilent Feature Extraction Software. Two different statistical methods were used to determine differentially expressed genes: mixed ANOVA (MxANOVA) and significance analysis of microarrays (SAM). The list of differentially expressed genes in each comparison group was analyzed for statistically enriched or depleted biological classifications using the GoMiner database engine.

Equal numbers of Tsc2ang1 cells were seeded in three T-75 flasks and treated with Vehicle control, rapamycin, imatinib or imatinib and rapamycin for 24 hours. RNA was extracted and purified using QIAGEN RNeasy Mini Kit (no. 74104) and quantified spectrophotometrically. RNA (1 µg) was used after DNase treatment (no. 18068-015; Invitrogen) followed by first-strand cDNA synthesis and RT-PCR (no. 12371-019; SuperScript, Invitrogen) using a 96-well Optical Reaction Plate (no. 128; ABI PRISM, Applied Biosystems) for the RT-PCR reaction. A measure of 2.5 µl of template, which had been diluted 1:10 in molecular grade water (Cellgro; Mediatech Inc.) was used and each data point was set in in triplicate. Angpt2, Nrarp, Vegf, Aurora kinase A, Aurora kinase B, Centromere protein A, Cyclin B1 and 18S TaqMan Gene Expression primer assay from Applied Biosystems were used along with master mix (TaqMan Fast Universal PCR Master Mix [2×]; Applied Biosystems). The reaction was run on the 7500 Applied Biosystems Reader for absolute quantification for 96-well plates. Gene expression data were automatically calculated by Sequence Detection Software, version 1.3.1 (Applied Biosystems) as mean+/−SEM.

Example 4

Transcriptional Profiling Analysis

Figure 4A:
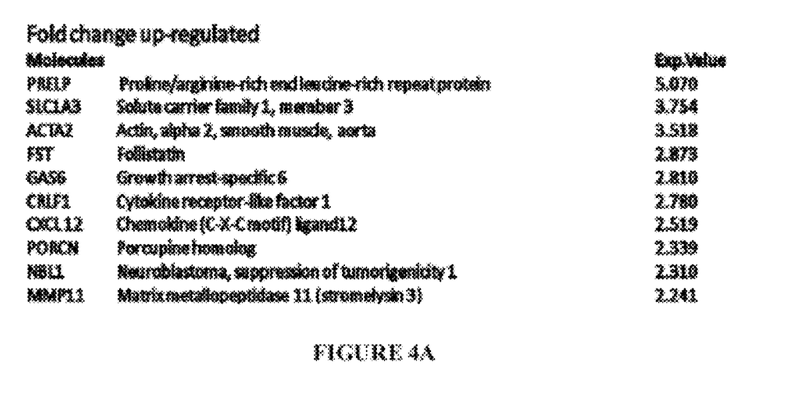
Figure 4B:
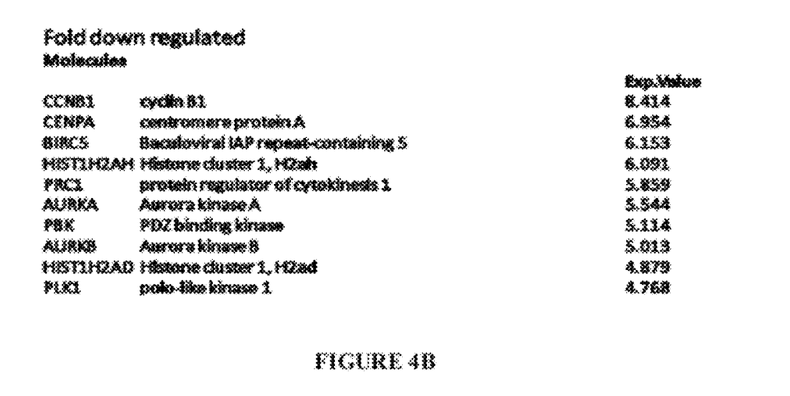

RNA was extracted from tsc2ang1 cells treated with rapamycin, imatinib and a combination of the two for 24 hours. A coordinate downregulation of Aurora kinase signaling pathway was seen in cells treated with rapamycin and imatinib combination therapy (FIG. 4a and FIG. 4b, showing change in gene expression) compared to vehicle control treatment.

Figure 5A:
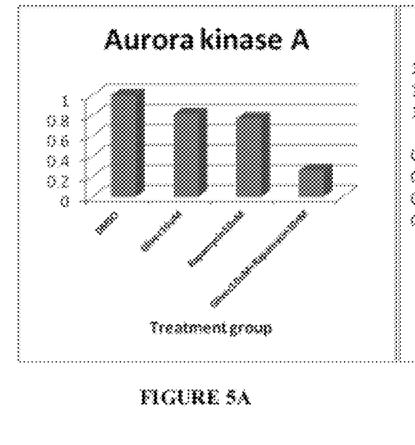
Figure 5B:
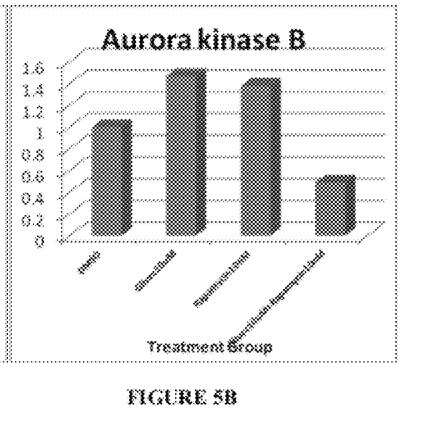
Figure 5C:
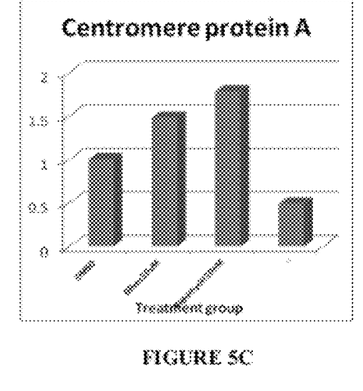
Figure 5D:
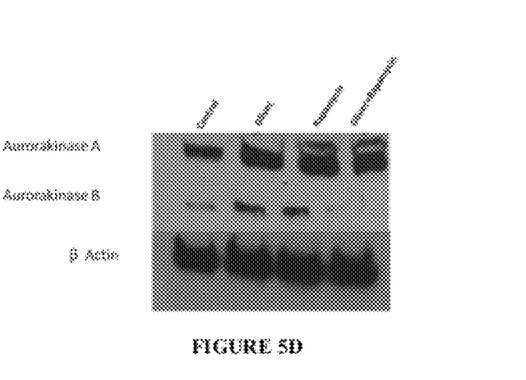

To verify the effect of imatinib and rapamycin on the levels of Aurora kinases A and B, imatinib (10 µM), rapamycin (10 nM), and a combination of both were tested in vitro with Tsc2ang1 cells. The combination therapy inhibited the relative expression levels of both Aurora kinase A (FIG. 5a) and Aurora kinase B (FIG. 5b) by 70% compared to DMSO treated control. The cells were also treated with the combination of imatinib (10 µM) and rapamycin (10 nM) for 24 hours before being lysed and analyzed by using antibodies specific for the Aurora kinase A and Aurora kinase B. βActin was used as the loading control by using monoclonal anti-β-Actin antibody. Western blot analysis (FIG. 5d) revealed that the combination therapy modestly increased the level of Aurora kinase A protein and caused a steep decrease in the level of Aurora kinase B protein.

Lysates of Tsc2ang1 cells treated with vehicle or indicated drugs were prepared in NP-40 lysis buffer (1% NP-40, 150 mmol/L NaCl, 10% glycerol, 20 mmol/L HEPES, 1 mmol/L phenylmethylsulfonyl fluoride, 2.5 mmol/L EDTA, 100 µmol/L Na3VO4, and 1% aprotinin) Protein concentration in cleared lysates was determined using an Eppendorf BioPhotometer. Samples were resolved using SDS-PAGE (National Diagnostics) and transferred to nitrocellulose membranes. The membranes were blocked with 5% nonfat dry milk in 10 mmol/L Tris/0.1% Tween 20/100 mmol/L NaCl and incubated with primary antibodies followed by horseradish peroxidase-conjugated secondary antibody. The immunoreactive bands were visualized by enhanced chemiluminescence (Amersham Biosciences). The antibodies used were: Phospho-PDGFR-β antibody (Tyr 1021) (Cell signaling Laboratories); Phospho-PDGFR-β antibody (Tyr 1009) (Cell Signaling Laboratories); Aurora kinase A antibody (4718) (Cell signaling Laboratories), Aurorakinase B (3094) antibody (Cell signaling Laboratories) monoclonal anti-β-tubulin antibody (Sigma) was used as a loading control.

Example 5

Matrix Metalloproteinase Activity

Figure 6:
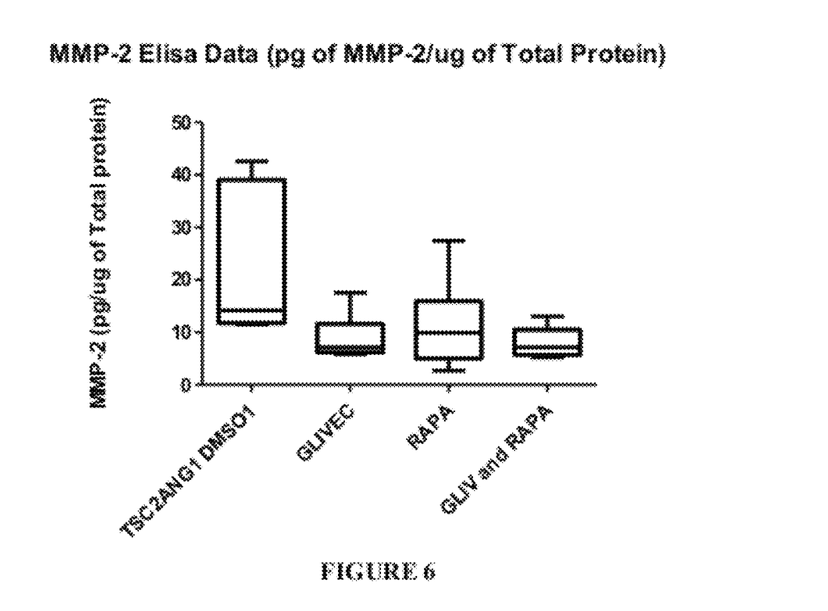
FIG. 6. Substrate gel electrophoresis using gelatin as the substrate.

The matrix metalloproteinase (MMP) activity of tsc2ang1 cells treated with either imatinib or rapamycin monotherapy showed a decrease in the level of MMP-2 compared with control. A greater reduction in the MMP bioactivity, however, was found when the cells were treated with imatinib and rapamycin in combination (FIG. 6). Specifically, substrate gel electrophoresis using gelatin as the substrate indicated that the treatment of tsc2ang1 cells with rapamycin, imatinib, and a combination of rapamycin and imatinib for 24 hours resulted in a decrease in the gelatinase activity of MMP-2 (~65 kDa) in comparison to control (DMSO-treated) treatment.

The presence and activity of specific MMP species were detected using gelatin zymography. An aliquot of each conditioned media sample was centrifuged at 4,000 rpm for 1-5 min at 4° C. and supernatant was used. A buffer of 4% SDS, 0.15 mol/L Tris (pH 6.8), 20% glycerol and 0.5% (w/v) bromophenol blue was added to the conditioned media sample. Condition media samples mixed with buffer were directly added to 10% SDS-acrylamide gel containing 0.1% (w/v) gelatin (BioRad) and separated by running on a mini gel apparatus at 15 mA/gel, and then gels gently rocked in a 2.5% Triton X-100 solution for 30 min at room temperature. Gels were then incubated over night at 37° C. in substrate buffer containing 50 mmol/L Tris-HCL (pH 8), 5 mmol/L CaCl2 and 0.02% NaN3. After incubation, gels were stained for 30 min in 0.5% Coomassie Blue R-250 dissolved in acetic acid, isopropyl alcohol and water (1:3:6); destained in acetic acid, ethanol and water (1:3:6). The finalized gel was scored for the presence/absence MMP activity by a blinded evaluator and photographed.

Example 6

Effect of Therapy on FoxM1

Figure 7:
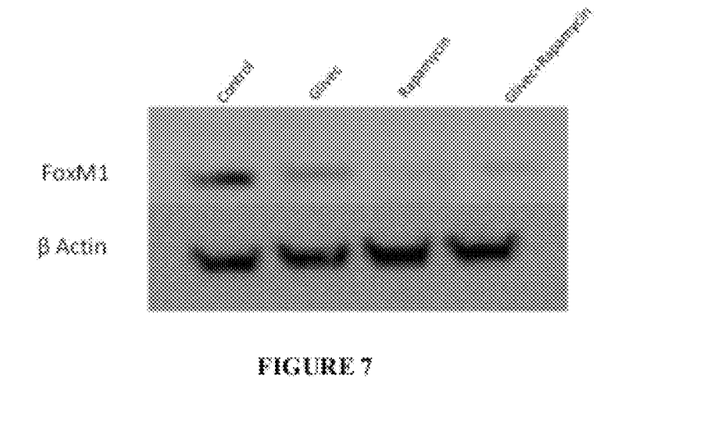
FIG. 7. Western blot analysis using FoxM1 monoclonal antibody.

In order to understand the differential effect of combination therapy on Aurora kinase B over Aurora kinase A, FoxM1 expression was examined. FoxM1 is a transcription factor that is required for the expression of Aurora kinase B but not Aurora kinase A. Combination therapy of tsc2ang1 cells with imatinib (10 μM) and rapamycin (10 nM) for 24 hours resulted in the downregulation of FoxM1 protein compared with DMSO control (FIG. 7). This was determined by western blot analysis using a FoxM1 monoclonal antibody following cell lysis. βActin was used as the loading control by using a monoclonal anti-β-Actin antibody.

Example 7

In Vivo Tumorigenesis

Figure 8A:
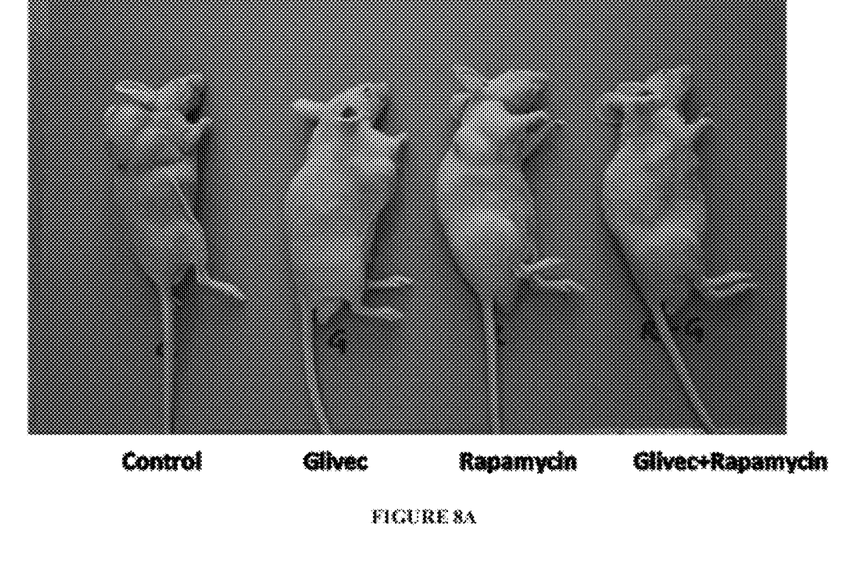
FIG. 8. Effect of sirolimus and imatinib on in vivo growth of tsc2ang1 xenografts in nude mice.

To determine whether compounds that inhibit VEGF, phosphorylated forms of PDGFR-β, and angiopoietin 2 in vitro would affect tumor formation in vivo, $10^6$ Tsc2ang1 cells were injected subcutaneously into nude mice (n=4) in each treatment group. Two days later, intraperitoneal treatment with control, imatinib, rapamycin, and combination therapy of imatinib and rapamycin was conducted for 30 days. The treatment resulted in a 97% decreased tumor volume in the imatinib and rapamycin combination treatment group compared with control (FIG. 8).

Figure 8B:
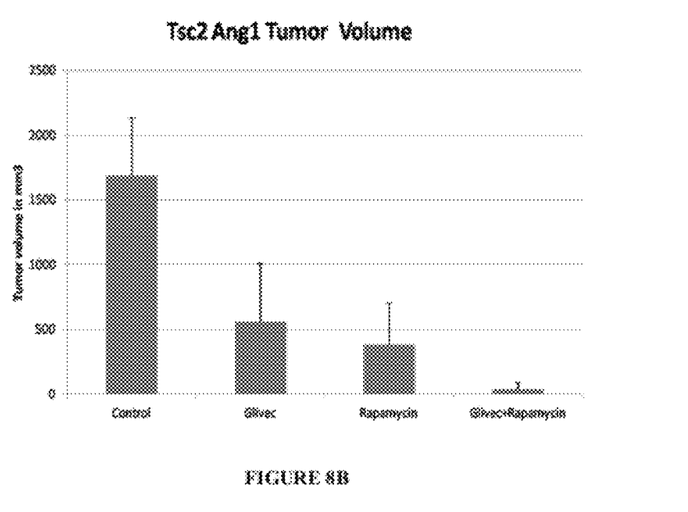

The compounds were suspended in 0.1 ml of ethanol and 0.9 ml of Intralipid solution (Fresenius Kabi, Uppsala, Sweden). No local or systemic toxicity was observed in any of the animals. Injections were given over a period of 4 weeks, after which the mice were sacrificed due to overwhelming tumor burden in the control group. Date are presented as average tumor volume (mm3) in each of the two groups vs. controls with bars representing SEM. A representative vehicle-treated mouse is shown on the left (FIG. 8a), and a representative treated mouse is shown on the right (FIG. 8b). The y-axis represents tumor volume and the x-axis treatment. Column 1 represents vehicle-treated mice (n=3), and column 2, 3 and 4 represent imatinib, rapamycin, and combination therapy of imatinib and rapamycin (n=4), respectively. P=0.076 using the two-tailed t test.

Example 8

Sirolimus and Imatinib combination Therapy for Tuberous Sclerosis

A subject diagnosed with tuberous sclerosis will be treated with a combination therapy comprising sirolimus and imatinib. Specifically, the subject will be treated with Rapamune and Gleevec. The treatment will comprise an initial bolus of 6 mg Rapamune followed by 2 mg daily as well as 400 mg Gleevec daily. Potential toxicity resulting from the treatment will be monitored during said treatment. This combination therapy will result in a reduction of the tumor volume associated with tuberous sclerosis in the subject.

What is claimed:

1. A method of treating tuberous sclerosis comprising administering an effective amount of sirolimus in combination with imatinib to a subject in need thereof.
2. The method of claim 1, wherein the subject is diagnosed with a mutation in hamartin (tsc1) or tuberin (tsc2).
3. The method of claim 1, wherein imatinib is administered to a human subject orally at about 400 mg, 600 mg, or 800 mg per day.
4. The method of claim 1, wherein sirolimus is administered to a human subject orally at a dose of about 0.5 mg, 1 mg, or 2 mg per day.
5. The method of claim 1, wherein the subject has autism.
6. The method of claim 1, wherein the subject has seizures.

* * * * *